United States Patent
Klug et al.

(10) Patent No.: US 9,592,185 B2
(45) Date of Patent: Mar. 14, 2017

(54) COMPOSITIONS CONTAINING HYDROGEN PEROXIDE OR SUBSTANCES RELEASING HYDROGEN PEROXIDE

(75) Inventors: Peter Klug, Grossostheim (DE); Maurice Frederic Pilz, Frankfurt am Main (DE); Ute Back, Blankenbach (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 13/994,337

(22) PCT Filed: Dec. 13, 2011

(86) PCT No.: PCT/EP2011/006277
§ 371 (c)(1),
(2), (4) Date: Jun. 14, 2013

(87) PCT Pub. No.: WO2012/079739
PCT Pub. Date: Jun. 21, 2012

(65) Prior Publication Data
US 2013/0272984 A1    Oct. 17, 2013

(30) Foreign Application Priority Data
Dec. 17, 2010   (DE) .............. 10 2010 054 866

(51) Int. Cl.
| | | |
|---|---|---|
| *A61K 8/49* | (2006.01) | |
| *A61K 8/22* | (2006.01) | |
| *A61Q 5/04* | (2006.01) | |
| *A61Q 5/08* | (2006.01) | |
| *A61Q 5/10* | (2006.01) | |
| *C01B 15/037* | (2006.01) | |
| *C01B 15/08* | (2006.01) | |
| *C01B 15/12* | (2006.01) | |
| *C07D 213/89* | (2006.01) | |
| *C11D 3/28* | (2006.01) | |
| *C11D 3/32* | (2006.01) | |
| *C11D 3/39* | (2006.01) | |
| *C11D 7/32* | (2006.01) | |
| *D06L 3/02* | (2006.01) | |

(52) U.S. Cl.
CPC .............. *A61K 8/4926* (2013.01); *A61K 8/22* (2013.01); *A61Q 5/04* (2013.01); *A61Q 5/08* (2013.01); *A61Q 5/10* (2013.01); *C01B 15/037* (2013.01); *C01B 15/085* (2013.01); *C01B 15/123* (2013.01); *C07D 213/89* (2013.01); *C11D 3/28* (2013.01); *C11D 3/32* (2013.01); *C11D 3/394* (2013.01); *C11D 3/3947* (2013.01); *C11D 7/3281* (2013.01); *D06L 3/021* (2013.01); *A61K 2800/30* (2013.01)

(58) Field of Classification Search
CPC ........ A61K 8/22; A61K 2800/30; D06L 3/021
USPC .............................. 424/62; 252/186; 510/375
See application file for complete search history.

(56) References Cited

U.S. PATENT DOCUMENTS

| | | | |
|---|---|---|---|
| 4,804,705 A | 2/1989 | Pum et al. | |
| 5,206,385 A | 4/1993 | Login et al. | |
| 6,083,422 A | 7/2000 | Ambuter et al. | |
| 6,180,118 B1 | 1/2001 | Maubru | |
| 2004/0074015 A1 | 4/2004 | Kravtchenko et al. | |
| 2004/0191202 A1* | 9/2004 | Murad ................ | 424/70.13 |
| 2006/0009371 A1 | 1/2006 | Wang et al. | |
| 2007/0199160 A1* | 8/2007 | Pasquier .............. | A61K 8/49 |
| | | | 8/405 |
| 2011/0003010 A1 | 1/2011 | Klug et al. | |
| 2013/0236383 A1 | 9/2013 | Klug et al. | |
| 2014/0147402 A1 | 5/2014 | Klug et al. | |

FOREIGN PATENT DOCUMENTS

| | | | | |
|---|---|---|---|---|
| DE | 102010054918 | | 6/2011 | |
| EP | 0 829 258 | | 3/1998 | |
| EP | 1 347 736 | | 7/2002 | |
| FR | 2 804 863 | | 8/2001 | |
| GB | 2 207 501 | * | 1/1989 | ............... A61K 7/06 |
| WO | WO 02/051369 | | 7/2002 | |
| WO | WO 02/051961 | | 7/2002 | |
| WO | WO 2009/015856 | | 2/2009 | |

OTHER PUBLICATIONS

ChemMatters, Title: pH & hair; pp. 8-9, published Apr. 1982.*
English Abstract for DE102010054918, dated Jun. 30, 2011.
English Abstract for FR 2 804 863, dated Aug. 17, 2001.
Karlheinz Schrader, Andreas Domsch, Cosmetology—Theory and Practice, vol. II, Verlag für chemische Industrie, Augsburg, 2005, pp. 114-115.
Karlheinz Schrader, Andreas Domsch, Cosmetology—Theory and Practice, vol. II, Verlag für chemische Industrie, Augsburg, 2005, p. 145.
International Search Report for PCT/EP2011/003537, dated Mar. 6, 2012.
International Preliminary Report on Patentability for PCT/EP2011/003537, dated Jan. 29, 2013.
International Search Report for PCT/EP2011/003536, dated Mar. 5, 2012.
International Preliminary Report on Patentability for PCT/EP2011/003536, dated Feb. 14, 2013.
International Search Report for PCT/EP2011/006277, dated Mar. 5, 2012.
International Preliminary Report on Patentability for PCT/EP2011/006277, dated Jun. 20, 2013.

* cited by examiner

*Primary Examiner* — Yanzhi Zhang
(74) *Attorney, Agent, or Firm* — Tod A. Waldrop

(57) ABSTRACT

The invention relates to compositions containing a) one or more substances selected from the group of hydrogen peroxide and substances releasing hydrogen peroxide, b) water, d) one or more substances selected from the group consisting of hydroxypyridones and the salts thereof, characterized in that said compositions do not comprise polymers having thickening properties. The compositions are particularly characterized by the advantageous storage stability thereof.

11 Claims, No Drawings

COMPOSITIONS CONTAINING HYDROGEN PEROXIDE OR SUBSTANCES RELEASING HYDROGEN PEROXIDE

The present invention relates to compositions comprising hydrogen peroxide or hydrogen peroxide-releasing substances.

Aqueous compositions comprising hydrogen peroxide are utilized in various applications. They are used in cosmetic compositions, for example as a bleaching composition for hair, as a developer component in hair dyes, but also as a component for hair setting in permanent wave formulations. Further applications are, for example, tooth bleaching compositions. In industrial cleaning and in domestic cleaning and in textile bleaching too, acidic, hydrogen peroxide-containing compositions are present in cleaner formulations.

However, the stability of the hydrogen peroxide or of the hydrogen peroxide-releasing substances in compositions which do not comprise any thickening polymers is often unsatisfactory.

The literature cites various stabilizers for hydrogen peroxide; for example, EP 1 347 736 discloses oxidative compositions for hair treatment, these comprising stabilizers based on pyrophosphate, stannates, phenacetin or oxyquinoline, or combinations thereof. However, these compositions also comprise polymers having thickening properties.

It was therefore an object of the present invention to provide compositions of long-term storage stability which comprise hydrogen peroxide and/or hydrogen peroxide-releasing substances, but no polymers having thickening properties.

It has now been found that, surprisingly, this object is achieved by incorporating hydroxypyridones or salts thereof into aqueous compositions which comprise one or more substances selected from the group consisting of hydrogen peroxide and hydrogen peroxide-releasing substances but do not comprise any polymers having thickening properties.

The invention therefore provides compositions comprising a) one or more substances selected from the group consisting of hydrogen peroxide and hydrogen peroxide-releasing substances,
b) water,
d) one or more substances selected from the group consisting of hydroxypyridones and salts thereof,
wherein the compositions do not comprise any polymer having thickening properties.

The inventive compositions now also make it possible to obtain low-viscosity compositions comprising hydrogen peroxide and/or hydrogen peroxide-releasing substances with elevated stability. Low-viscosity compositions are required, for example, in the sector of cleaner formulations or else of textile bleaching. The increased stability of the hydrogen peroxide and/or of the hydrogen peroxide-releasing substances in these compositions can achieve improved cleaning or bleaching performance.

Preferably, the one or more substances of component a) are selected from the group consisting of hydrogen peroxide, urea peroxide, perborates, persulfates and mixtures thereof. More preferably, the substance of component a) is hydrogen peroxide.

The one or more substances selected from the group consisting of hydrogen peroxide and hydrogen peroxide-releasing substances of component a) are present in the inventive compositions preferably in amounts of 0.5 to 20% by weight, more preferably in amounts of 1 to 10% by weight, especially preferably in amounts of 1.5 to 7% by weight and exceptionally preferably in amounts of 2 to 7% by weight, based on the total weight of the compositions. Among these, the substance of component a) is again preferably hydrogen peroxide, which is present in the inventive compositions preferably in amounts of 0.5 to 20% by weight, more preferably in amounts of 1 to 10% by weight, especially preferably in amounts of 1.5 to 7% by weight and exceptionally preferably in amounts of 2 to 7% by weight, based on the total weight of the compositions.

In a preferred embodiment of the invention, the water (component b)) is present in the inventive compositions in an amount of 40% by weight or more and preferably in an amount of 50% by weight or more, based on the total weight of the compositions.

Polymers having thickening properties are, in the context of the present invention, preferably understood to mean polymeric materials which have a molecular weight above 5000 g/mol and are suitable for significantly thickening a composition comprising one or more substances selected from the group consisting of hydrogen peroxide and hydrogen peroxide-releasing substances with use amounts of the polymer of 30% by weight or less, preferably of 10% by weight or less, more preferably of 6% by weight or less and especially preferably of 3% by weight or less, based on the total weight of the composition. This thickening is preferably such that the viscosity of the composition in mPa·s at 20° C. is increased by 30% or more with the abovementioned amounts of the polymers.

The viscosity of the inventive compositions is preferably ≤2000 mPa·s at 20° C., more preferably ≤1000 mPa·s at 20° C. and especially preferably ≤500 mPa·s at 20° C. The viscosities are measured on the inventive compositions themselves with a Brookfield viscometer model DV II at 20 revolutions/minute and 20° C. The spindles from the RV spindle set are used. Under these measurement conditions, spindle 1 is selected for viscosities not exceeding 500 mPa·s, spindle 2 for viscosities not exceeding 1000 mPa·s, and spindle 3 for viscosities not exceeding 5000 mPa·s.

Preferably, the inventive compositions do not comprise any polymers.

Preferably, the one or more substances of component d) are selected from compounds of the formula (I) and salts thereof

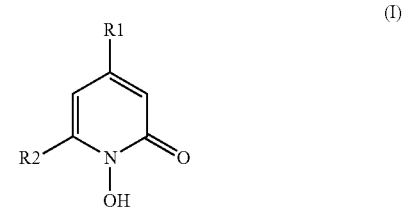

(I)

in which R1 is H or a $C_1$-$C_4$ alkyl radical and R2 is H, an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_6$-$C_{10}$ aryl radical or an unsubstituted or halogen-substituted, branched or unbranched $C_7$-$C_{20}$ aralkyl radical.

The R2 radicals are preferably not halogen-substituted.

In a preferred embodiment of the invention, the one or more compounds of component d) are present in the inventive compositions in the form of the acid (compounds of the formula (I)) or in the form of the alkali metal, alkaline earth metal or amine salts thereof, or salts thereof with polymeric counterions.

R1 in the one or more compounds of the formula (I) or in the salts thereof is preferably methyl, and R2 is preferably cyclohexyl or 2,4,4-trimethylpentyl.

More preferably, the compounds of the formula (I) are in the form of the alkanolamine salts thereof and especially preferably in the form of the monoethanolamine salts thereof. Examples of such salts are mentioned in DE 2234009.

Particular preference is given to 4-methyl-6-(2,4,4-trimethylpentyl)-1-hydroxy-2-pyridone, the monoethanolamine salt of 4-methyl-6-(2,4,4-trimethylpentyl)-1-hydroxy-2-pyridone (Octopirox®, Clariant), and 4-methyl-6-(cyclohexyl)-1-hydroxy-2-pyridone and the monoethanolamine salt of 4-methyl-6-(cyclohexyl)-1-hydroxy-2-pyridone (Ciclopirox®, Sanofi-Aventis).

These substances can be obtained by methods known from the literature; cf. the references cited in DE 2234009.

In the inventive compositions, the one or more substances of component d) are present in amounts of preferably 0.1 to 20 000 ppm (0.00001 to 2% by weight), more preferably in amounts of 0.5 to 1000 ppm (0.00005 to 0.1% by weight) and especially preferably in amounts of 0.5 to 100 ppm (0.00005 to 0.01% by weight), based on the total weight of the compositions.

The hydroxypyridones can be combined in the inventive compositions with further stabilizers. Further suitable stabilizers are, for example, polyphosphates and the alkali metal or alkaline earth metal salts thereof, alkali metal or alkaline earth metal stannates, phenacetin and the acid salts thereof, and oxyquinoline and the acid salts thereof. In general, the hydrogen peroxide solutions ready for delivery already comprise stabilizers, preferably in the form of polyphosphates.

The inventive compositions can be used as bleaching compositions for hair or teeth, as a bleaching component or developer for oxidative hair dyes or as a fixing component for permanent wave formulations and as a domestic cleaner. In addition, the inventive compositions can be used, for example, as prewash sprays, stain removers, surface cleaners or toilet cleaners. A further possible use is that of hair coloring compositions for prevention of bleaching damage in the course of hair coloring.

In a further preferred embodiment of the invention, the inventive compositions are emulsions. The emulsions are preferably oil-in-water emulsions or microemulsions.

The nonaqueous component of these emulsions, which is composed substantially of the emulsifier and the oil body, is typically 0.5 to 20.0% by weight and preferably 1.0 to 10.0% by weight, based on the total weight of the emulsions. It follows from this that the emulsions may contain 80.0 to 99.5% by weight and preferably 90.0 to 99.0% by weight of the aqueous phase, based on the total weight of the emulsions.

The inventive compositions may also comprise anionic, cationic, nonionic, ampholytic surfactants and/or betaine surfactants.

The total amount of the surfactants used in the inventive compositions is, based on the total weight of the compositions, preferably from 0.1 to 20% by weight, more preferably from 0.5 to 10.0% by weight and especially preferably from 1.0 to 5.0% by weight.

Preferred anionic surfactants are $(C_{10}-C_{22})$-alkyl and -alkylene carboxylates, alkyl ether carboxylates, fatty alcohol sulfates, fatty alcohol ether sulfates, alkylamide sulfates and sulfonates, alkanesulfonates and hydroxyalkanesulfonates, olefinsulfonates, acyl esters of isethionates, $\alpha$-sulfo fatty acid esters, alkylbenzenesulfonates, alkylphenol glycol ether sulfonates, sulfosuccinates, sulfosuccinic monoesters and diesters, fatty alcohol phosphates, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates, acyl glutamates and acyl glycinates. These compounds and mixtures thereof are utilized in the form of the water-soluble or water-dispersible salts thereof, for example the sodium, potassium, magnesium, ammonium, mono-, di- and triethanolammonium, and analogous alkylammonium salts.

The amount of the anionic surfactants in the inventive compositions is preferably from 0.05 to 20.0% by weight, more preferably from 0.5 to 10.0% by weight and especially preferably from 1.0 to 5.0% by weight, based on the total weight of the compositions.

Preferred cationic surfactants are quaternary ammonium salts, such as di($C_8$-$C_{22}$)-alkyldimethylammonium chloride or bromide, preferably di($C_8$-$C_{22}$)-alkyldimethylammonium chloride or bromide; ($C_8$-$C_{22}$)-alkyl-dimethylethylammonium chloride or bromide; ($C_8$-$C_{22}$)-alkyltrimethylammonium chloride or bromide, preferably cetyltrimethylammonium chloride or bromide and ($C_8$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyldimethylbenzylammonium chloride, ($C_8$-$C_{22}$)-alkyl-dimethylhydroxyethylammonium chloride, phosphate, sulfate or lactate, ($C_8$-$C_{22}$)-alkylamidopropyltrimethylammonium chloride or methosulfate, N,N-bis(2-$C_8$-$C_{22}$-alkanoyloxyethyl)dimethylammonium chloride or methosulfate, N,N-bis(2-$C_8$-$C_{22}$-alkanoyloxyethyl)hydroxyethylmethyl-ammonium chloride or methosulfate, and ester quats based on $C_8$-$C_{22}$ alkanoyl esters of triethanolamine or methyldiethanolamine.

The amount of the cationic surfactants in the inventive compositions is preferably from 0.1 to 10.0% by weight, more preferably from 0.5 to 7.0% by weight and especially preferably from 1.0 to 5.0% by weight, based on the total weight of the compositions.

Preferred nonionic surfactants are, for example, fatty acid alkanolamides; sucrose esters; sorbitol esters and sorbitan esters, and also $C_8$-$C_{22}$-alkyl polyglucosides.

The amount of the nonionic surfactants in the inventive compositions (for example in the case of rinse-off products) is preferably in the range from 0.05 to 20.0% by weight, more preferably from 0.1 to 10.0% by weight and especially preferably from 0.5 to 5.0% by weight, based on the total weight of the compositions.

In addition, the inventive compositions may comprise amphoteric surfactants. These can be described as derivatives of long-chain secondary or tertiary amines which have an alkyl group with 8 to 18 carbon atoms and in which a further group is substituted by an anionic group which imparts solubility in water, thus, for example, by a carboxyl, sulfate or sulfonate group. Preferred amphoteric surfactants are N—($C_{12}$-$C_{18}$)-alkyl-$\beta$-amino-propionates and N—($C_{12}$-$C_{18}$)-alkyl-$\beta$-iminodipropionates as alkali metal and mono-, di- and trialkylammonium salts; suitable further surfactants are also amine oxides. These are oxides of tertiary amines with a long-chain group having 8 to 18 carbon atoms and two mostly short-chain alkyl groups having 1 to 4 carbon atoms. Preference is given here, for example, to the $C_{10}$- to $C_{18}$-alkyldimethylamine oxides, fatty acid amidoalkyldimethylamine oxide.

A further preferred group of surfactants is that of betaine surfactants, also known as zwitterionic surfactants. These contain, in the same molecule, a cationic group, especially an ammonium group, and an anionic group, which may be a carboxylate group, sulfate group or sulfonate group. Suitable betaines are preferably alkylbetaines such as cocobetaine or fatty acid alkylamidopropyl betaines, for example cocoacylamidopropyl dimethyl betaine or the $C_{12}$- to $C_{18}$-dimethylaminohexanoates and/or the $C_{10}$- to $C_{18}$-acylamidopropane dimethyl betaines.

The amount of the amphoteric surfactants and/or betaine surfactants in the inventive compositions is preferably from 0.5 to 20.0% by weight and more preferably from 1.0 to 10.0% by weight, based on the total weight of the compositions.

Preferred surfactants are lauryl sulfate, laureth sulfate, cocoamidopropyl betaine, alkyl betaines such as cocobetaine, amine oxides, sodium cocoylglutamate and lauroamphoacetate.

The inventive compositions may comprise, as further assistants and additives, for example, oil bodies, waxes, emulsifiers, coemulsifiers, solubilizers, superfatting agents, refatting agents, active antimicrobial ingredients, humectants, solvents, dyes, fragrances, pearlizing agents and/or opacifiers.

The oil bodies may advantageously be selected from the groups of triglycerides, natural and synthetic fatty substances, preferably esters of fatty acids with alcohols of low carbon number, for example with isopropanol, propylene glycol or glycerol, or esters of fatty alcohols with alkanoic acids of low carbon number or with fatty acids or from the group of alkyl benzoates, and also natural or synthetic hydrocarbon oils.

Useful substances include triglycerides of linear or branched, saturated or unsaturated, optionally hydroxylated, $C_8$-$C_{30}$-fatty acids, in particular vegetable oils, such as sunflower oil, corn oil, soybean oil, rice oil, jojoba oil, babassu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, e.g. the commercial product Myritol® 318. Hydrogenated triglycerides are also preferred in accordance with the invention. Oils of animal origin, for example beef tallow, perhydrosqualene, lanolin, can also be used.

A further class of preferred oil bodies is that of the benzoic esters of linear or branched $C_{8-22}$-alkanols, e.g. the commercial products Finsolv® SB (isostearyl benzoate), Finsolv® TN ($C_{12}$-$C_{15}$-alkyl benzoate) and Finsolv® EB (ethylhexyl benzoate).

A further class of preferred oil bodies is that of the dialkyl ethers having a total of 12 to 36 carbon atoms, especially having 12 to 24 carbon atoms, for example di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and di-tert-butyl ether and diisopentyl ether.

Likewise useful are branched saturated or unsaturated fatty alcohols having 6-30 carbon atoms, e.g. isostearyl alcohol, and Guerbet alcohols.

A further class of preferred oil bodies is that of alkyl hydroxycarboxylates. Preferred alkyl hydroxycarboxylates are full esters of glycolic acid, lactic acid, malic acid, tartaric acid or citric acid. Further esters of hydroxy-carboxylic acids which are suitable in principle are esters of β-hydroxypropionic acid, of tartronic acid, of D-gluconic acid, sugar acid, mucic acid or glucuronic acid. Suitable alcohol components of these esters are primary, linear or branched aliphatic alcohols having 8 to 22 carbon atoms. The esters of $C_{12}$-$C_{15}$-fatty alcohols are particularly preferred. Esters of this type are commercially available, e.g. under the trade name Cosmacol® from EniChem, Augusta Industriale.

A further class of preferred oil bodies is that of dicarboxylic esters of linear or branched $C_2$-$C_{10}$-alkanols, such as di-n-butyl adipate (Cetiol® B), di(2-ethylhexyl) adipate and di(2-ethylhexyl) succinate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate, and also diisotridecyl azelate.

Likewise preferred oil bodies are symmetrical, asymmetrical or cyclic esters of carbonic acid with fatty alcohols, glycerol carbonate or dicaprylyl carbonate (Cetiol® CC).

A further class of preferred oil bodies is that of the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols.

A further class of preferred oil bodies is that of hydrocarbon oils, for example those with linear or branched, saturated or unsaturated $C_7$-$C_{40}$-carbon chains, for example Vaseline, dodecane, isododecane, cholesterol, lanolin, synthetic hydrocarbons, hexadecane, isohexadecane, paraffin oils, isoparaffin oils, e.g. the commercial products of the Permethyl® series, squalane, squalene, and alicyclic hydrocarbons, e.g. the commercial product 1,3-di(2-ethylhexyl) cyclohexane (Cetiol® S), ozokerite, and ceresine.

The inventive compositions may comprise waxes, for example paraffin waxes, microwaxes and ozokerites, beeswax and its component fractions, beeswax derivatives, and natural waxes such as rice wax, candelilla wax, carnauba wax, japan wax or shellac wax.

Emulsifiers, coemulsifiers and solubilizers which may be used are nonionic, anionic, cationic or amphoteric surface-active compounds.

Useful nonionogenic surface-active compounds are preferably:
fatty alcohols having 8 to 22 carbon atoms, glycerol mono- and diesters and sorbitan mono- and diesters of saturated and unsaturated fatty acids having 6 to 22 carbon atoms; polyol esters; fatty acid amides, fatty acid alkanolamides and mixtures of compounds of two or more of these substance classes.

Suitable ionogenic coemulsifiers are, for example, anionic emulsifiers, such as mono-, di- or triphosphoric acid esters, soaps (e.g. sodium stearate), fatty alcohol sulfates, but also cationic emulsifiers such as mono-, di- and trialkyl quats.

Available amphoteric emulsifiers are preferably alkylaminoalkylcarboxylic acids, betaines, sulfo betaines and imidazoline derivatives.

Particularly advantageous coemulsifiers are glyceryl monostearate, glyceryl monooleate, diglyceryl monostearate, glyceryl isostearate, glycol distearate, sorbitan monoisostearate, sorbitan stearate, sorbitan oleate, sucrose distearate, lecithin, cetyl alcohol, stearyl alcohol, behenyl alcohol and isobehenyl alcohol.

The inventive compositions may comprise one or more of the emulsifiers, coemulsifiers or solubilizers in amounts of 0.1 to 20.0% by weight, preferably of 1.0 to 15.0% by weight and more preferably of 3.0% to 10.0% by weight, based on the total weight of the compositions.

Superfatting agents which may be used are preferably lanolin and lecithin, nonethoxylated lanolin derivatives and lecithin derivatives or acylated lanolin derivatives and lecithin derivatives, polyol fatty acid esters, mono-, di- and triglycerides and/or fatty acid alkanolamides, where the latter simultaneously serve as foam stabilizers, which are preferably used in amounts of 0.01% to 10.0% by weight, more preferably of 0.1% to 5.0% by weight and especially preferably of 0.5% to 3.0% by weight, based on the total weight of the compositions.

Antimicrobial active ingredients which may be used are cetyltrimethylammonium chloride, cetylpyridinium chloride, benzethonium chloride, diisobutylethoxyethyldimethylbenzylammonium chloride, sodium aluminum chlorohydroxylactate, triethyl citrate, 2,4,4'-trichloro-2'-hydroxydiphenyl ether (triclosan), 3,4,4'-trichlorocarbanilide (triclocarban), diaminoalkyl-amide, for example L-lysine hexadecylamide, citrate heavy metal salts, salicylates, pyrithiones and heavy metal salts thereof, especially zinc pyrithione, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide, iodopropynyl butylcarbamate, methylchloroisothiazolinone, methyl-isothiazolinone, methyldibromoglutaronitrile, AgCl, chloroxylenol, sodium benzoate, and phenoxyethanol, phenoxyisopropanol, parabens, preferably butyl, ethyl, methyl and propyl paraben, and sodium salts thereof, pentanediol, 1,2-hexanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), sodium salt of hydroxymethylglycinate.

The inventive compositions comprise the active antimicrobial ingredients preferably in amounts from 0.001% to 5.0% by weight, more preferably from 0.01% to 3.0% by weight, and with particular preference from 0.1% to 2.0% by weight, based on the total weight of the compositions.

In addition, it is possible to use humectants selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxy acids, panthenol and derivatives thereof, for example D-panthenol (R-2,4-dihydroxy-N-(3-hydroxypropyl)-3,3-dimethylbutamide), DL-panthenol, calcium pantothenate, panthetine, pantotheine, panthenyl ethyl ether, isopropyl palmitate, glycerol and/or sorbitol, preferably in amounts of from 0.1% to 15.0% by weight and particularly preferably from 0.5% to 5.0% by weight, based on the total weight of the compositions.

Additionally, the inventive compositions may comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, tert-butanol, glycerol, 1,2-propanediol and 1,3-propanediol, and mixtures of said alcohols. Further suitable solvents are, for example, triacetin (glycerol triacetate) and 1-methoxy-2-propanol.

The inventive compositions may comprise dyes and pigments, either organic or inorganic dyes selected from the corresponding positive list of the German Cosmetics Act or from the EC list of cosmetic colorants.

| Chemical or other name | CIN | Color |
| --- | --- | --- |
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Cerise Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfonic acid diethylamide-1'-phenylazo)-3-hydroxy-5''-chloro-2'',4''-dimethoxy-2-naphthanilide | 12490 | red |
| Disperse Yellow 16 | 12700 | yellow |
| 1-(4-Sulfo-1-phenylazo)-4-aminobenzenesulfonic acid | 13015 | yellow |
| 2,4-Dihydroxyazobenzene-4'-sulfonic acid | 14270 | orange |
| 2-(2,4-Dimethylphenylazo-5-sulfonic acid)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonic acid-4-chloro-5-carboxylic acid-1-phenylazo)-2-hydroxynaphthalene | 15525 | red |
| 1-(3-Methylphenylazo-4-sulfonic acid)-2-hydroxynaphthalene | 15580 | red |
| 1-(4',(8')-Sulfonic acid naphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |

-continued

| Chemical or other name | CIN | Color |
|---|---|---|
| 1-(2-Sulfo-4-methyl-5-chloro-1-phenylazo)-2-hydroxy-naphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4'-[(4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-Carotenealdehyde ($C_{30}$) | 40820 | orange |
| trans-Apo-8'-Carotenic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenyl-carbinol | 42051 | blue |
| 4-[(4-N-Ethyl-p-sulfobenzylamino)phenyl-(4-hydroxy-2-sulfophenyl)(methylene)-1-(N-ethyl-N-p-sulfobenzyl)-2,5-cyclohexadieneimine] | 42053 | green |
| Acid Blue 7 | 42080 | blue |
| (N-Ethyl-p-sulfobenzylaminophenyl-(2-sulfophenyl)-methylene-(N-ethyl-N-p-sulfobenzyl)cyclohexa-dieneimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4''-(N-diethyl)amino-2-methyl-N-ethyl-N-m-sulfobenzyl-fuchsonimmonium | 42735 | blue |
| 4'-(N-Dimethyl)amino-4''-(N-phenyl)aminonaphtho-N-dimethylfuchsonimmonium | 44045 | blue |
| 2-Hydroxy-3,6-disulfo-4,4'-bisdimethylaminonaphtho-fuchsinimmonium | 44090 | green |
| Acid red | 45100 | red |
| 3-(2'-Methylphenylamino)-6-(2'-methyl-4'-sulfophenyl-amino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |

-continued

| Chemical or other name | CIN | Color |
|---|---|---|
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidine)anthraquinone | 61570 | green |
| Acid Blue 80 | 61585 | blue |
| Acid Blue 62 | 62045 | blue |
| N,N'-Dihydro-1,2,1',2'-anthraquinoneazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha, beta- or gamma-Carotene | 75130 | orange |
| Keto and/or hydroxyl derivatives of carotene | 75135 | yellow |
| Guanine or pearlescent agents | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of the chlorophylls and chlorophyllines | 75810 | green |
| Aluminum | 77000 | white |
| Aluminum hydrate | 77002 | white |
| Water-containing aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromic oxide | 77288 | green |
| Chromium oxide, hydrated | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxides and hydroxides | 77491 | red |
| Hydrated iron oxide | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Caramel | | brown |
| Capsanthin, Capsorubin | | orange |
| Betanine | | red |
| Benzopyrilium salts, anthocyanines | | red |
| Aluminum, zinc, magnesium and calcium stearate | | white |
| Bromothymol Blue | | blue |
| Bromocresol Green | | green |
| Acid Red 195 | | red |

Also advantageous are oil-soluble natural dyes, for example paprika extracts, β-carotene and cochineal.

Fragrance and/or perfume oils which may be used are individual odorant compounds, e.g. the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ethers, the aldehydes include, for example, the linear alkanals having 8 to 18 carbon atoms, citral, citronellol, citronellyloxyacetaldehyde, cyclamenaldehyde, hydroxycitronellal, lilial and bourgeonal, the ketones include, for example, the ionones, alpha-isomethylionone and methyl cedryl ketone, the alcohols include anethol, citronellol, eugenol, geraniol, linalool, phenylethyl alcohol and terpineol, and the hydrocarbons include primarily the terpenes and balsams. Preference is given to using mixtures of different odorants which together produce a pleasing scent note.

Perfume oils may also comprise natural odorant mixtures, as are accessible from vegetable or animal sources, e.g. pine oil, citrus oil, jasmine oil, lily oil, rose oil or ylang-ylang oil. Essential oils of relatively low volatility which are usually used as aromatic components are also suitable as perfume oils, e.g. sage oil, chamomile oil, clove oil, melissa oil, mint oil, cinnamon leaf oil, linden blossom oil, juniperberry oil, vetiver oil, olibanum oil, galbanum oil and ladanum oil.

Preferentially suitable pearlizing components are fatty acid monoalkanol-amides, fatty acid dialkanolamides, monoesters or diesters of alkylene glycols, in particular ethylene glycol and/or propylene glycol, with higher fatty acids, such as, for example, palmitic acid, stearic acid and behenic acid, monoesters or polyesters of glycerol with carboxylic acids, fatty acids and metal salts thereof, ketosulfones or mixtures of the specified compounds. Particular preference is given to ethylene glycol distearates and/or polyethylene glycol distearates having an average of 3 glycol units.

If the inventive compositions comprise pearlizing compounds, these are preferably present in the inventive compositions in an amount of 0.1 to 15.0% by weight and more preferably in an amount of 1.0 to 10.0% by weight, based on the total weight of the compositions.

The acids or alkalis used for pH adjustment are preferably mineral acids, more particularly HCl, inorganic bases, especially NaOH or KOH, and organic acids, especially citric acid.

The inventive compositions preferably have a pH of 2 to 11, more preferably from 7 to 11, more preferably from 8 to 11 and especially preferably from 8.5 to 11.

In a further preferred embodiment of the invention, the inventive compositions are compositions for bleaching and/or coloring of hair or a permanent wave formulation.

In a further preferred embodiment of the invention, the inventive compositions are oxidative cleaner formulations.

In a further preferred embodiment of the invention, the inventive compositions are compositions for oxidative bleaching of fibers or textiles.

The inventive compositions are advantageously suitable for reducing hair damage in hair coloring formulations.

The examples and applications which follow are intended to illustrate the invention in detail, but without restricting it thereto. All percentages are % by weight (% by wt.), unless explicitly stated otherwise.

TEST EXAMPLES

Example 1

Hydrogen peroxide solution from Solvay (35% by weight in water) or from Merck (35% by weight in water) was diluted with demineralized water to a hydrogen peroxide content of about 6.0% by weight and adjusted to a pH of 9.0 with sodium hydroxide solution (20% by weight). Further solutions were each additized with 8 ppm of 4-methyl-6-(2,4,4-trimethylpentyl)-1-hydroxy-2-pyridone (additive A, dissolved in propylene glycol). The solutions were stored at room temperature (20° C.) and 40° C. for 1 week and the hydrogen peroxide content was measured before and after storage (see Table 1).

TABLE 1

Results of the measurement of the hydrogen peroxide content

| Hydrogen peroxide | Additive A | Hydrogen peroxide content immediate [% by wt.] | Hydrogen peroxide content after 1 week at 20° C. [% by wt.] | Hydrogen peroxide content after 1 week at 40° C. [% by wt.] |
|---|---|---|---|---|
| Solvay (35% by wt.) | no | 6.3 | 4.8 | <0.1 |
| Solvay (35% by wt.) | yes | 6.0 | 6.1 | 5.9 |
| Merck (35% by wt.) | no | 5.9 | 3.9 | 2.0 |
| Merck (35% by wt.) | yes | 6.1 | 6.1 | 5.8 |

Example 2

Hydrogen peroxide solution from Solvay (35% by weight in water) or from Merck (35% by weight in water), a solution of sodium $C_{14-17}$ alkyl sec-sulfonates (Hostapur® SAS 30) and demineralized water were mixed so as to result in a hydrogen peroxide content of about 6.0% by weight and a content of sodium $C_{14-17}$ alkyl sec-sulfonates of 5.0% by weight. Thereafter, sodium hydroxide solution (20% by weight) was used to establish a pH of 9.0. Further solutions were each additized with 7 ppm of 4-methyl-6-(2,4,4-trimethylpentyl)-1-hydroxy-2-pyridone (additive A, dissolved in propylene glycol). The solutions were stored at room temperature and 40° C. for 1 week and the hydrogen peroxide content was measured before and after storage (see Table 2).

TABLE 2

Results of the measurement of the hydrogen peroxide content

| Hydrogen peroxide | Additive A | Hydrogen peroxide content immediate [% by wt.] | Hydrogen peroxide content after 1 week at 20° C. [% by wt.] | Hydrogen peroxide content after 1 week at 40° C. [% by wt.] |
|---|---|---|---|---|
| Solvay (35% by wt.) | no | 6.1 | 3.7 | 0.1 |
| Solvay (35% by wt.) | yes | 6.0 | 6.1 | 5.8 |
| Merck (35% by wt.) | no | 5.9 | 4.2 | 1.4 |
| Merck (35% by wt.) | yes | 6.0 | 6.1 | 5.2 |

The results of examples 1 and 2 show that 4-methyl-6-(2,4,4-trimethylpentyl)-1-hydroxy-2-pyridone can significantly enhance the storage stability of hydrogen peroxide solutions at high pH both at room temperature and at 40° C.

FORMULATION EXAMPLES

Formulation Example 1

Prewash Spray for Laundry

| Ingredient | % by wt. |
|---|---|
| hydrogen peroxide (35% by wt., aqueous) | 10.0 |
| Decyl Glucoside (50% by wt. aqueous solution) | 5.0 |
| Coco Glucoside (50% by wt. aqueous solution) | 2.0 |
| Hostapur ® SAS 60 (Sodium C14-17 Alkyl Sec Sulfonate) | 5.0 |
| 4-methyl-6-(2,4,4-trimethylpentyl)-1-hydroxy-2-pyridone, monoethanolamine salt | 0.0005 |
| propylene glycol | 1.0 |
| water | ad 100 |

Production:
4-Methyl-6-(2,4,4-trimethylpentyl)-1-hydroxy-2-pyridone monoethanolamine salt (Octopirox®) is dissolved in propylene glycol. The surfactants are dissolved in water, the hydrogen peroxide solution and the propylene glycol solution are introduced, and the mixture is homogenized. The product is adjusted to pH=4.

Formulation Example 2

Stain Remover

| Ingredient | % by wt. |
|---|---|
| hydrogen peroxide (35% by wt., aqueous) | 10.0 |
| Sodium C14-17 Olefin Sulfonate | 5.0 |
| 4-methyl-6-(cyclohexyl)-1-hydroxy-2-pyridone | 0.0005 |
| propylene glycol | 1.0 |
| water | ad 100 |

Production:
4-Methyl-6-(cyclohexyl)-1-hydroxy-2-pyridone is dissolved in propylene glycol. The surfactant is dissolved in water, the hydrogen peroxide solution and the propylene glycol solution are introduced, and the mixture is homogenized. The product is adjusted to pH=7.

Formulation Example 3

Stain Remover

| Ingredient | % by wt. |
|---|---|
| hydrogen peroxide (35% by wt., aqueous) | 12.0 |
| Lauryl Glucoside (50% by wt. aqueous solution) | 7.0 |
| 4-methyl-6-(2,4,4-trimethylpentyl)-1-hydroxy-2-pyridone | 0.0005 |
| propylene glycol | 1.0 |
| MEA dodecylbenzenesulfonate | 6.0 |
| water | ad 100 |

Production:
4-Methyl-6-(2,4,4-trimethylpentyl)-1-hydroxy-2-pyridone is dissolved in propylene glycol.
The surfactants are dissolved in water, the hydrogen peroxide solution and the propylene glycol solution are introduced, and the mixture is homogenized. The product is adjusted to pH=4.7.

The invention claimed is:

1. A composition comprising
   a) at least one substance selected from the group consisting of hydrogen peroxide and hydrogen peroxide-releasing substances,
   b) water, and
   d) at least one substance selected from the group consisting of compounds of the formula (I) and salts thereof

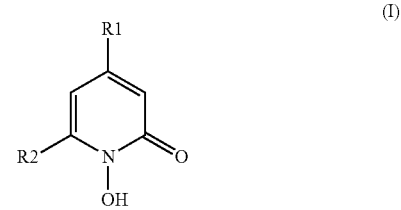

(I)

in which R1 is H or a $C_1$-$C_4$ alkyl radical and R2 is H, an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_6$-$C_{10}$ aryl radical or an unsubstituted or halogen-substituted, branched or unbranched $C_7$-$C_{20}$ aralkyl radical,
wherein the composition further comprises active antimicrobial ingredients in amounts from 0.001% to 5.0% by weight, based on the total weight of the composition, with the proviso that the composition does not comprise any polymer having thickening properties.

2. The composition as claimed in claim 1, wherein the at least one substance of component a) is selected from the group consisting of hydrogen peroxide, urea peroxide, perborates, persulfates and mixtures thereof.

3. The composition as claimed in claim 1, wherein the substance of component a) is hydrogen peroxide and the hydrogen peroxide is present in the composition in amounts of 0.5 to 20% by weight based on the total weight of the composition.

4. The composition as claimed in claim 1, wherein the at least one compound of component d) is present in the form of an acid or in the form of an alkali metal, alkaline earth metal, or amine salt thereof.

5. The composition as claimed in claim 1, wherein, in the at least one compound of the formula (I) or in the salts thereof, R1 is methyl and R2 is cyclohexyl or 2,4,4-trimethylpentyl.

6. The composition as claimed in claim 1, which comprises the at least one substance of component d) in amounts of 0.1 ppm to 2% by weight, based on the total weight of the composition.

7. The composition as claimed in claim 6, which comprises the at least one substance of component d) in amounts of 0.5 to 100 ppm, based on the total weight of the composition.

8. The composition as claimed in claim 1, which has a pH of 2 to 11.

9. The composition as claimed in claim 8, which has a pH of 7 to 11.

10. An oxidative cleaner formulation comprising at least one composition according to claim 1.

11. A composition for oxidative bleaching of fibers or textiles comprising at least one composition according to claim 1.

* * * * *